United States Patent [19]

Guttmann et al.

[11]  4,316,856

[45]  Feb. 23, 1982

[54] MOLYBDENUM-PROMOTED ANTIMONY PHOSPHATE OXIDE COMPLEX CATALYSTS ALSO CONTAINING AT LEAST ONE OF BISMUTH AND TELLURIUM

[75] Inventors: Andrew T. Guttmann, Maple Heights; Robert K. Grasselli, Chagrin Falls, both of Ohio

[73] Assignee: The Standard Oil Co., Cleveland, Ohio

[21] Appl. No.: 108,327

[22] Filed: Dec. 28, 1979

[51] Int. Cl.$^3$ ............ C07C 120/14; C07C 120/00
[52] U.S. Cl. ............ 260/465.3; 260/465.9; 568/477; 585/433; 585/628; 585/630; 252/437
[58] Field of Search ............ 260/465.3, 465.9

[56] References Cited

U.S. PATENT DOCUMENTS

| | | | |
|---|---|---|---|
| 3,346,617 | 10/1967 | Hiroki et al. | 260/465.3 |
| 3,426,060 | 2/1969 | Eden | 260/465.3 |
| 3,541,129 | 11/1970 | Yamada et al. | 260/465.3 |
| 3,542,843 | 11/1970 | Yoshino et al. | 260/465.3 |
| 3,546,138 | 12/1970 | Callahan et al. | 252/456 |
| 4,000,176 | 12/1976 | Yoshino et al. | 260/465.3 |

*Primary Examiner*—Joseph Paul Brust
*Attorney, Agent, or Firm*—John E. Miller, Jr.; Herbert D. Knudsen; Larry W. Evans

[57] ABSTRACT

Molybdenum-promoted antimony phosphates also containing at least one of tellurium and bismuth have been found to exhibit significant catalytic activity in various oxidation-type reactions.

5 Claims, No Drawings

MOLYBDENUM-PROMOTED ANTIMONY PHOSPHATE OXIDE COMPLEX CATALYSTS ALSO CONTAINING AT LEAST ONE OF BISMUTH AND TELLURIUM

BACKGROUND OF THE INVENTION

The present invention relates to new oxide complex catalysts for use in various oxidation-type reactions.

Oxide complexes of varying different compositions have been found to exhibit catalytic activity in different types of oxidation reactions, such as for example the oxidation of olefins to produce acids and aldehydes, the ammoxidation of olefins to produce unsaturated nitriles and the oxydehydrogenation of olefins to produce di-olefins. As is known, such oxide complexes are relatively complex structures the exact nature of which is not understood. In operation, such catalysts continuously lose and gain oxygen and hence they are often referred to as redox catalysts.

It is an object of the present invention to provide a new type of oxide complex redox catalyst useful in a wide variety of different oxidation-type reactions.

SUMMARY OF THE INVENTION

This and other objects are accomplished by the present invention which is based on the discovery that oxide complex catalysts comprising antimony phosphates containing molybdenum and at least one of tellurium and bismuth provide significant catalytic activity in various oxidation-type reactions.

Thus, the present invention provides novel catalysts for use in various types of oxidation-type reactions, comprising oxide complexes of the formula:

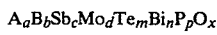

wherein
A is one or more elements selected from the group of alkali metals, alkaline earth metals, and thallium;
B is one or more elements selected from the group of Fe, Co, Ni, Mn, Cr, Zn, Cd and B; and
wherein
a is 0–1;
b is 0–1;
c is 8–10;
d is 0.1–2;
p is 7.0–9.9;
m is 0–1;
n is 0–1;
(m+n)>0; and
x is a number which satisfies the valence requirements of the other elements present.

In addition, the present invention provides improvements in the known processes for the oxidation of various olefins to produce aldehydes and acids, the ammoxidation of olefins, alcohols and aldehydes to produce the corresponding nitriles and the oxydehydrogenation of various olefins to produce diolefins and aromatics, the improvements in accordance with the present invention comprising using as the catalyst in said processes an oxide complex of the formula:

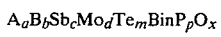

wherein

A is one or more elements selected from the group of alkali metals, alkaline earth metals, and thallium;
B is one or more elements selected from the group of Fe, Co, Ni, Mn, Cr, Zn, Cd and B; and
a is 0–1;
b is 0–1;
c is 8–10;
d is 0.1–2;
p is 7.0–9.9;
m is 0–1;
n is 0–1;
(m+n)>0; and
x is a number which satisfies the valence requirements of the other elements present.

DETAILED DESCRIPTION

Catalysts

The inventive oxide complex catalysts are described as catalyst systems containing antimony phosphate as catalyst host lattice, the host lattice being promoted with molybdenum, at least one of bismuth and tellurium, and optionally a number of other elements. A major portion (and preferably at least 80%) of the oxide complex exhibits the known layer structure of $SbPO_4$ as described, for example, in B. Kinberger, Act. Chem. Scand. 1970, 24 (1), 320-8 (Eng.), CA 72, 115581 m. Thus, preferably, the Sb/P ratio varies between 0.7/1 to 1/0.7, more preferably between 0.8/1 to 1/0.8. These catalysts can be represented by the formula:

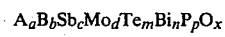

wherein
A is one or more elements selected from the group of alkali metals, alkaline earth metals, and thallium;
B is one or more elements selected from the group of Fe, Co, Ni, Mn, Cr, Zn, Cd and B; and
a is 0–1;
b is 0–1;
c is 8–10;
d is 0.1–2;
p is 7.0–9.9;
m is 0–1;
n is 0–1;
(m+n)>0; and
x is a number which satisfies the valence requirements of the other elements present.

Preferred catalysts are those which contain tellurium, those which are free of copper and especially those which are both free of copper and contain tellurium. If the catalyst contains tellurium, the preferred Mo/Te is 1/1 to 20/1, preferably 2/1 to 5/1, more preferably 3 to 4.5, and within these groups it is preferable that d+m is 0.2 to 1.0, preferably 0.4 to 0.8, based on an antimony content of 10. Moveover, while some of the antimony in the catalyst can be present in the pentavalent state, it is preferable that most, and more preferable all, of the antimony is in the trivalent state.

The inventive oxide complex catalyst can be used either in unsupported form or supported on a suitable support. Any conventional support such as silica, alumina, titania, zeolites, Alundum, natural clays and so forth can be employed as supports. The preferred support is silica. Moreover, if silica is used, it is preferred that the dry colloidal form of silica (e.g. Aerosil or Cabosil) be used in the catalyst preparation.

The catalysts of the present invention can be prepared by techniques adapted from the known $SbPO_4$ synthesis from phosphoric acid and $Sb_2O_3$ disclosed in Robbins, J. Inorg. Nuclear Chem. 19, 183–5 (1961). See also British Pat. No. 792,997. One general technique involves dissolving compounds of the catalytic elements in hot $H_3PO_4$, followed by the addition of silica or other support and $Sb_2O_3$, digestion drying and calcination. Digestion can occur for 30 minutes to 10 hours at 50° C. to 100° C. while calcination can occur for $\frac{1}{2}$ to 50 hours at 400° C. to 800° C. Compounds used to supply the elements of the catalyst can be any compounds of the type normally used during catalyst preparation. For example, ammonium heptamolybdate can be used to supply molybdenum while 12-molybdophosphoric acid can be used to supply both molybdenum and phosphorus. $TeO_2$ can be used to supply tellurium, $Sb_2O_3$ to supply antimony and the other metals can be supplied in the form of nitrates and/or acetates. Pentavalent antimony can be supplied in the form of antimony pentachloride or other pentavalent antimony compound. Details of other modified procedures for preparing catalysts in accordance with the present invention can be found in the working examples.

Ammoxidation

A wide variety of different reactants can be ammoxidized in accordance with the present invention to produce nitriles. For example, olefins such as propylene and isobutylene, alcohols such as t-butyl alcohol, and aldehydes such as acrolein and methacrolein can be readily converted to nitriles in accordance with the present invention. In general, compounds which can be converted to nitriles by the inventive ammoxidation reaction include 3 to 9 carbon hydrocarbons unsubstituted or substituted with oxygen or hydroxy. Preferred starting materials are olefins, aldehydes and alcohols containing 3 or 4 carbon atoms.

The general ammoxidation process for converting olefins, alcohols and aldehydes to nitriles is well known. See, for example, U.S. Pat. No. 3,546,138, the disclosure of which is incorporated herein by reference. In general, the ammoxidation reaction is accomplished by contacting the reactant, oxygen and ammonia with a particular catalyst in the vapor phase. The inventive reaction is carried out in the same manner and under the conditions generally set forth in this patent.

In a preferred aspect, the inventive process comprises contacting a mixture comprising propylene or isobutylene, ammonia and oxygen with the promoted catalyst of this invention at an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give similar results. The molar ratio of oxygen to the olefin in the feed to the reaction vessel should be in the range of 0.5:1 to 4.1 and a ratio of about 1:1 to 3:1 is preferred.

Low molecular weight saturated hydrocarbons do not appear to influence the reaction to an appreciable degree, and these materials can be present; consequently, the addition of saturated hydrocarbons to the reaction feed is contemplated within the scope of this invention. Likewise, diluents, such as nitrogen and the oxides of carbon, may be present in the reaction mixture without deleterious effect.

The molar ratio of ammonia to olefin in the feed to the reactor may vary between about 0.05:1 to 5:1. There is no real upper limit for the ammonia/olefin ratio, but there is generally no reason to exceed the 5:1 ratio. At ammonia/olefin ratios appreciably less than the stoichiometric ratio of 1:1, various amounts of oxygenated derivatives of the olefin will be formed.

Significant amounts of unsaturated aldehydes, as well as nitriles, will be obtained at ammonia-olefin ratios substantially below 1:1, i.e., in the range of 0.15:1 to 0.75:1. Above the upper limit of this range, the amount of aldehydes produced rapidly decreases. It is fortuitous that within the ammonia-olefin range stated, maximum utilization of ammonia is obtained and this is highly desirable. It is generally possible to recycle any unreacted olefin and unconverted ammonia.

Water can also be included in the feed although it is not essential. In some instances, e.g. fixed-bed systems, water may improve the selectivity of the reaction and the yield of nitrile. However, reactions not including water in the feed are also within the scope of the present invention.

In general, the molar ratio of added water to olefin, when water is added, is in the neighborhood of 0.1:1 or higher. Ratios on the order of 1:1 to 3:1 are particularly desirable, but higher ratios may be employed, i.e. up to about 10:1.

The reaction is carried out at an elevated temperature such as 200° C. to 600° C., preferably 400° C. to 500° C. The pressure at which the reaction is conducted is also an important variable, and the reaction should be carried out at about atmospheric or slightly above atmospheric (2 to 3 atmospheres) pressure. In general, high pressures, i.e. above 15 atmospheres, are not suitable since higher pressures tend to favor the formation of undesirable byproducts.

The apparent contact time is not critical, and contact times in the range of from 0.1–50 seconds may be employed. The optimal contact time will, of course, vary depending upon the reactant being used, but in general, contact time of from 1–15 seconds is preferred.

The inventive ammoxidation reaction is carried out in the vapor phase. Normally, the process is conducted on a continuous basis using either a fixed-bed or a fluid-bed catalyst. However, a batch operation can be employed.

The reaction product passing out of the reactor is normally in the form of a gas. Conventionally, this gaseous reaction product is treated to remove $NH_3$ and then partially condensed either by indirect contact with a cooling medium or direct contact with water to form a liquid phase containing acrylonitrile, acrolein, acrylic acid, HCN and acetonitrile and a vapor phase containing $CO_2$, CO, $N_2$ and $O_2$. The acrylonitrile is then separated from the liquid phase by a number of different techniques such as, for example, distillation or water extraction/distillation. Additional steps can be employed to separately recover HCN and/or acetonitrile from the gross reaction product.

Oxidation

As previously indicated, the catalysts of this invention can also be employed in the catalytic oxidation of olefins to various different reaction products.

The reactants used in the oxidation to oxygenated compounds are oxygen and an olefin such as propylene, isobutylene and other olefins having up to three contiguous carbon atoms (i.e. three carbon atoms arranged in a straight chain).

The olefins may be in admixture with paraffinic hydrocarbons, such as ethane, propane, butane and pentane; for example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e. 0.1 to 10 atmospheres, temperatures in the range of 150° C. to 600° C. may be advantageously employed. However, the process may be conducted at other pressures, and in the case where superatmospheric pressures, e.g. above 10 atmospheres are employed, somewhat lower temperatures are possible. In the case where this process is employed to convert propylene to acrolein, a temperature range of 200° C. to 500° C. has been found to be optimum at atmospheric pressure.

While pressures other than atmospheric may be employed, it is generally preferred to operate at or near atmospheric prressure, since the reaction proceeds well at such pressures and the use of expensive high pressure equipment is avoided, and formation of undesired by-products and waste is diminished.

The apparent contact time employed in the process is not critical and it may be selected from a broad operable range which may vary from 0.1 to 50 seconds. The apparent contact time may be defined as the length of time in seconds which a unit volume of gas measured under the conditions of reaction is in contact with the apparent unit volume of the catalyst. It may be calculated, for example, from the apparent volume of the catalyst bed, the average temperature and pressure of the reactor, and the flow rates of the several components of the reaction mixture.

The optimum contact time will, of course, vary depending upon the olefin being treated, but in the case of propylene and isobutylene, the preferred contact time is 0.15 to 15 seconds.

A molar ratio of oxygen to olefin between about 0.5:1 to 5:1 generally gives the most satisfactory results. For the conversion of propylene to acrolein, a preferred ratio of oxygen to olefin is from about 1:1 to about 2.5:1. The oxygen used in the process may be derived from any source; however, air is the least expensive source of oxygen and is preferred for that reason.

The addition of water to the reaction mixture in oxidation reactions can have a beneficial influence on the conversion and yields of the desired product especially in fixed-bed reactions. The manner in which water affects the reaction is not fully understood. In any event, it is preferred in fixed-bed operation to include water in the reaction mixture, and in general a ratio of olefin to water in the reaction mixture of from 1:1.25 to 1:10 will give very satisfactory results while a ratio of 1:0.5 to 1:6 has been found the optimum when converting propylene to acrolein.

Inert diluents such as oxygen and carbon dioxide, may be present in the reaction mixture.

Oxydehydrogenation

In accordance with the present invention, the promoted catalyst system of the present invention can also be employed in the catalytic oxidative dehydrogenation of olefins to diolefins and aromatic compounds. In this process, the feed stream in vapor form containing the olefin to be dehydrogenated and oxygen is conducted over the promoted catalyst at a comparatively low temperature to obtain the corresponding diolefin.

By the term "olefin" as used herein is meant open chain as well as cyclic olefins. The olefins dehydrogenated in accordance with this invention have at least four and up to about nine nonquaternary carbon atoms, of which at least four are arranged in series in a straight chain or ring. The olefins preferably are either normal straight chain or tertiary olefins. Both cis and trans isomers, where they exist, can be dehydrogenated.

Among the many olefinic compounds which can be dehydrogenated in this way are butene-1; butene-2; pentene-1; pentene-2; pentenes, hexenes, etc. such as 2-methyl-pentene-1, 3-methylbutene-1, 3,4-dimethylpentene-1, 4-methyl-pentene-2; heptene-1; octene-1; cyclopentene; cyclohexene, 3-methyl cyclohexene and cycloheptene.

Open chain olefins yield diolefins, and, in general, six-membered ring olefins yield aromatic ring compounds. The higher molecular weight open chain olefins may cyclize to aromatic ring compounds.

The feed stock in addition to the olefin and oxygen can contain one or more paraffins or naphthenic hydrocarbons having up to about ten carbon atoms, which may be present as impurities in some petroleum hydrocarbon stocks and which may also be dehydrogenated in some cases.

The amount of oxygen can be within the range of from about 0.3 to about 4 moles per mole of double-bond created. Stoichiometrically, 0.5 mole of oxygen is required for the dehydrogenation of one mole of monolefin to a diolefin. It is preferred to employ an excess of oxygen, e.g. an oxygen/olefin ratio of from 0.6 to about 3, in order to ensure a higher yield of diolefin per pass. The oxygen can be supplied as pure or substantially pure oxygen or as air.

When pure oxygen is used, it may be desirable to incorporate a diluent in the mixture such as steam, carbon dioxide or nitrogen.

The feed stock can be catalytically dehydrogenated in the presence of steam, but this is not essential. When steam is used, from about 0.1 to about 6 moles of steam per mole of olefin reactant is employed, but amounts larger than this can be used.

The dehydrogenation proceeds at temperatures within the range of from about 300° C. to about 1,000° C. Optimum yields are obtainable at temperatures within the range from about 400° C. to 550° C.

The preferred reaction pressure is approximately atmospheric, within the range of from about 0.1 to about 5 atmospheres.

Only a brief contact time with the catalyst is required for effective dehydrogenation. The apparent contact time with the catalyst can vary from about 0.1 up to about 50 seconds but higher contact times can be used if desired. At these contact times, comparatively small reactors and small amounts of catalyst can be used effectively.

Process Conditions

In carrying out the foregoing processes, any apparatus of the type suitable for carrying out oxidation reactions in the vapor phase may be employed. The processes may be conducted either continuously or intermittantly. The catalyst may be a fixed-bed employing a large particulate or pelleted catalyst or, in the alternative, a fluid-bed catalyst may be employed.

WORKING EXAMPLES

In order to more thoroughly describe the present invention, the following working examples are presented. In these examples, various catalysts in accordance with the present invention were tested in the known ammoxidation reaction to produce acrylonitrile from propylene. In each example, 5 cc. of catalyst having a mesh size of 20 to 35 mesh was charged into a 5 cc. continuous flow fixed-bed micro-reactor and a feed comprising 1 propylene/1.2 $NH_3$/2.0 $O_2$/3.3 $H_2O$ was fed to the reactor at temperatures from 420° C. to 460° C. with contact times of from 6 to 9 seconds. The oxygen was supplied as air. The gross reaction product was recovered and analyzed, and the amounts of acrylonitrile and byproducts determined.

The catalysts were prepared by the general technique described above. As an example, the catalysts of Example 5 and comprising $Sb_{10}Mo_{0.3}Te_{0.1}P_{9.7}O_x$ supported on 20% silica were prepared in the following manner. 1.6 gms. phosphomolybdic acid was dissolved in 25.4 gms. 85% $H_3PO_4$ at 100° C. to 110° C., followed by the addition of 0.362 gms. $TeO_2$. The mixture was heated with stirring to 135° C., held 5 minutes at that temperature, cooled to 100° C. and diluted with 80 ml. water. Next, 12.5 gms. Aerosil 200 (dry colloidal silica) was stirred in at 60° C. to 70° C. 33.1 gms. $Sb_2O_3$ was then stirred in rapidly, and the mixture was held at 60° C. to 65° C. with stirring until it set-up to a putty (less than 1 hour). The mixture was then held in an oven at 60° C. to 65° C. for 4 to 5 hours, overnight at 120° C, and for 20 hours at 350° C. The dried material was then ground and screened to obtain a catalyst having a mesh size of 20 to 35 mesh, and the sample was then calcined for 5 hours at 500° C. to 600° C.

The compositions of the various catalysts employed, the final calcination temperature to which each catalyst is subjected, the reaction temperature, the contact time, the type of silica support used in the catalyst preparation and the results obtained are set forth in the following Tables I to IV. Unless otherwise indicated, all examples contained 20% silica as a support. In those experiments in which a 40% silica sol is used instead of Aerosil 200, the above preparation is modified in that the dilution of $H_3PO_4$ with water is omitted.

Examples 1 to 16 as set forth in the following Table I show the effect of tellurium and other promoters on the molybdenum-promoted antimony phosphates of the present invention.

TABLE I

SbPO$_4$-Based Catalysts Containing Molybdenum - C$_3$ Ammoxidation
Effect of Tellurium and Other Promoters
Reaction Temp. 420° C.; CT = 6 sec.; C$_3$/NH$_3$/O$_2$/H$_2$O = 1.0/1.2/2.0/3.2

| Example | Catalyst Composition | Heat Treatment (°C.) | Surface Area m$^2$/g. | % Conv. C$_3$ | % Yields AN | Aceto | HCN | CO$_x$ | % Select. AN |
|---|---|---|---|---|---|---|---|---|---|
| 1 | $Sb_{10}Mo_{0.3}P_{9.8}O_x$ | 525 | 31.8 | 31.5 | 12.6 | 9.0 | 2.3 | 7.5 | 40.1 |
| 2 | $Sb_{9.9}Cu_{0.2}Te_{0.1}Mo_{0.3}P_{9.7}O_x$ | 525 | | 65.4 | 40.3 | 4.7 | 0.9 | 16.7 | 61.6 |
| 3 | $Sb_{9.6}Cu_{0.5}Te_{0.5}Mo_{0.3}P_{9.5}O_x$ | 525 | | 62.2 | 28.2 | 4.6 | 0.0 | 15.0 | 19.7 |
| 4 | $Sb_{10}Mo_{0.1}Te_{0.033}P_{9.9}O_x$ | 525 | 29.9 | 40.8 | 19.6 | 11.0 | 3.0 | 7.0 | 48.0 |
| 5 | $Sb_{10}Mo_{0.3}Te_{0.1}P_{9.7}O_x$ | 525 | 30.9 | 77.8 | 55.5 | 5.6 | 4.4 | 9.7 | 71.4 |
| 6 | $Sb_{10}Mo_{0.6}Te_{0.2}P_{9.5}O_x$ | 525 | 26.1 | 69.9 | 30.1 | 2.0 | 1.0 | 11.3 | 43.0 |
| 7 | $Sb_{10}Mo_{12}Te_{0.4}P_{8.9}O_x$ | 525 | 10.7 | 70.8 | 32.9 | 1.9 | 0.5 | 16.3 | 46.5 |
| 8 | $Sb_{9.9}Bi_{0.1}Mo_{0.3}P_{9.8}O_x$ | 525 | | 43.2 | 12.1 | 13.8 | 3.5 | 13.7 | 28.1 |
| 9 | $Sb_{9.6}Bi_{0.1}Fe_{0.3}Mo_{0.3}P_{9.7}O_x$ | 525 | | 23.4 | 9.4 | 3.4 | 4.1 | 6.4 | 40.2 |
| 10 | $Sb_{9.7}Fe_{0.3}Mo_{0.3}Te_{0.1}P_{9.7}O_x$ | 525 | | 68.1 | 43.1 | 8.0 | 5.5 | 11.2 | 63.4 |
| 11 | $Sb_{9.7}U_{0.3}Mo_{0.3}Te_{0.1}P_{9.7}O_x$ | 525 | | 28.9 | 15.0 | 7.1 | 2.8 | 4.0 | 52.0 |
| 12 | $Sb_{9.8}Mn_{0.3}Mo_{0.3}Te_{0.1}P_{9.7}O_x$ | 525 | | 40.6 | 24.2 | 7.0 | 1.1 | 8.3 | 59.5 |
| 13 | $Sb_{9.7}Ce_{0.3}Mo_{0.3}Te_{0.1}P_{9.7}O_x$ | 525 | | 68.1 | 42.6 | 12.1 | 2.4 | 11.0 | 62.6 |
| 14 | $Sb_{9.7}Cr_{0.3}Mo_{0.3}Te_{0.1}P_{9.7}O_x$ | 525 | | 26.2 | 13.5 | 6.7 | 2.5 | 3.4 | 51.5 |
| 15 | $Sb_{10}Mo_{0.3}Te_{0.1}V_{0.3}P_{9.6}O_x$ | 525 | | 63.2 | 39.8 | 4.6 | 5.3 | 13.2 | 63.1 |
| 16 | $Sb_9Mo_{0.3}Te_{0.1}Sb^V P_{8.4}O_x$ | 525 | | 33.7 | 24.5 | 3.8 | 2.4 | 2.9 | 72.7 |

The above examples show that molybdenum-containing antimony phosphate exhibits significant catalytic activity in the production of acrylonitrile by the known ammoxidation reaction. In addition, these examples further show that these catalysts exhibit significantly improved catalytic activity if also containing bismuth or tellurium and optionally other promoting elements.

Examples 17 to 32 as set forth in the following Table II show the effect of using different silica sources during preparation of the catalysts as well as the effect of varying the amounts of molybdenum and tellurium.

TABLE II

SbPO$_4$-Based Catalysts Containing Mo and Te - C$_3$ Ammoxidation
Effect of Support - Aerosil vs. Silica Sol and the Amount of Mo and Te
Reaction Temp. 420° C.; C$_3$/NH$_3$/O$_2$/H$_2$O = 1.0/1.2/2.0/3.2

| Example | Catalyst Composition | Support | Heat Treat (°C.) | Surface Area m$^2$/g | CT sec | % Conv C$_3$ | % PPC AN | Aceto | HCN | CO$_x$ | % Sel AN | PN[3] |
|---|---|---|---|---|---|---|---|---|---|---|---|---|
| 17 | $Sb_{10}Mo_{0.3}Te_{0.1}P_{9.7}O_x$ | SOL[1] | 525 | 31 | 6 | 73.0 | 54.5 | 5.6 | 4.4 | 8.3 | 76.1 | 65 |
| 18 | " | SOL | 525 | 30 | 6 | 57.5 | 51.9 | 5.0 | 3.6 | 6.9 | 73.0 | 57 |
| 19 | " | Aerosil[2] | 525 | 48 | 6 | 97.9 | 69.6 | 9.1 | 4.1 | 14.7 | 71.0 | 70 |
| 20 | " | Aerosil | 600 | 38 | 6 | 94.8 | 69.6 | 5.6 | 5.1 | 14.0 | 73.4 | 72 |
| 21 | " | Aerosil | 600 | 38 | 9 | 98.1 | 60.9 | 14.3 | 4.2 | 16.2 | 62.1 | 62 |
| 22 | " | Aerosil | 525 | | 6 | 79.2 | 55.9 | 6.9 | 4.8 | 11.2 | 70.6 | 63 |
| 23 | " | Aerosil | 525 | | 9 | 92.5 | 62.4 | 7.4 | 5.0 | 7.3 | 78.3 | 75 |
| 24 | " | Aerosil | 600 | | 6 | 71.5 | 54.9 | 6.2 | 4.1 | 6.7 | 75.8 | 65 |
| 25 | " | Aerosil | 600 | | 9 | 88.3 | 57.7 | 12.3 | 3.3 | 13.3 | 65.4 | 62 |
| 26 | " | Aerosil | 525 | | 6 | 94.5 | 60.3 | 12.7 | 4.1 | 13.0 | 63.8 | 62 |
| 27 | " | Aerosil | 525 | | 9 | 96.9 | 64.6 | 7.9 | 3.3 | 17.8 | 66.7 | 66 |

TABLE II-continued

SbPO$_4$-Based Catalysts Containing Mo and Te - C$_3$ Ammoxidation
Effect of Support - Aerosil vs. Silica Sol and the Amount of Mo and Te
Reaction Temp. 420° C.; C$_3$/NH$_3$/O$_2$/H$_2$O = 1.0/1.2/2.0/3.2

| Example | Catalyst Composition | Support | Heat Treat (°C.) | Surface Area m$^2$/g | CT sec | % Conv C$_3$ | % PPC AN | Aceto | HCN | CO$_x$ | % Sel AN | PN[3] |
|---|---|---|---|---|---|---|---|---|---|---|---|---|
| 28 | Sb$_{10}$Mo$_{0.6}$Te$_{0.2}$P$_{9.5}$O$_x$ | Aerosil | 525 | | 6 | 94.2 | 58.8 | 2.7 | 4.3 | 17.9 | 62.4 | 61 |
| 29 | Sb$_{10}$Mo$_{0.6}$Te$_{0.1}$P$_{9.5}$O$_x$ | Aerosil | 525 | | 6 | 83.1 | 51.7 | 6.7 | 4.7 | 10.5 | 62.2 | 57 |
| 30 | Sb$_{10}$Mo$_{0.45}$Te$_{0.1}$P$_{9.6}$O$_x$ | Aerosil | 525 | | 6 | 89.6 | 59.6 | 6.6 | 4.4 | 12.4 | 66.6 | 63 |
| 31 | Sb$_{10}$Mo$_{0.2}$Te$_{0.2}$P$_{9.7}$O$_x$ | Aerosil | 525 | | 6 | 45.1 | 33.0 | 5.2 | 2.8 | 4.1 | 73.1 | 53 |
| 32 | Sb$_{10}$Mo$_{0.1}$Te$_{0.3}$P$_{9.7}$O$_x$ | Aerosil | 525 | | 6 | 39.4 | 25.7 | 6.8 | 2.3 | 4.5 | 65.2 | 45 |

[1] 20% SiO$_2$ as Nalco 40% sol, NH$_3$-stab.
[2] 20% Aerosil 200 (Degussa)
[3] Performance No. PN = (% ppc AN + % Select. AN)/2

The above Table II shows that catalysts made with Aerosil exhibit measurably better catalytic performance than those made with silica sols. In addition, these examples show that this effect is realized at varying molybdenum and tellurium levels.

Examples 33 to 53 as set forth in the following Table III show the effect of different preparation procedures, molybdenum sources and silica supports on the catalytic activity of catalysts produced in accordance with the present invention. All of the catalysts in these examples have the composition Sb$_{10}$Mo$_{0.3}$Te$_{0.1}$P$_{9.7}$O$_x$ plus 20% SiO$_2$, unless otherwise indicated. Most of these catalysts were prepared by the procedure described above in connection with Examples 1 to 16, and this preparation procedure is denoted in the following Table III as Preparation Procedure No. 1. Five additional preparation procedures were carried out as follows.

Procedure No. 2

A slurry of 12.5 gm. Aerosil 200 in 85 ml. H$_2$O was stirred and heated to 65° C. to 70° C. A solution of 1.20 gm. ammonium heptamolybdate in 5 ml. H$_2$O was added with continued agitation, followed by 0.362 gm. TeO$_2$ and 25.4 gm. 85% H$_3$PO$_4$. If stirring is difficult, more water can be added. After stirring for 5 to 7 minutes, 33.1 gm. Sb$_2$O$_3$ was mixed in thoroughly, and the mixture was stirred at approximately 65° C. until it set up to a putty (80 minutes). Further treatment was the same as in Procedure No. 1.

Procedure No. 3

Using the same reactants as in Procedure No. 2, the ammonium heptamolybdate was dissolved in 85 ml. H$_2$O, TeO$_2$ was added and dispersed by agitation, the mixture heated to 65° C., then the Aerosil stirred in. To the gelatinous slurry the H$_3$PO$_4$ was added slowly; then the Sb$_2$O$_3$ was stirred in and the mixture held at 65° C. It set up in 10 minutes. Further treatment as in Procedure No. 1.

Procedure No. 4

The mixture of ammonium heptamolybdate, TeO$_2$, Aerosil, and water was prepared as in Procedure No. 3. The slurry was then boiled in a covered beaker with additional 15 ml. H$_2$O for 1½ hours, cooled to 70° C., and H$_3$PO$_4$ and Sb$_2$O$_3$ added as in Procedure No. 3, followed by treatment as in Procedure No. 1.

Procedure No. 5

The mixture of ammonium heptamolybdate, TeO$_2$, Aerosil and water was prepared as in Procedure No. 3. It was then heated to approximately 95° C. with additional 20 ml. water, one third of the Sb$_2$O$_3$ was added and the mixture boiled for 1½ hours. The remainder of the Sb$_2$O$_3$ was then stirred in, the slurry cooled to 70° C., and the H$_3$PO$_4$ was added, followed by treatment as in Procedure No. 1.

Procedure No. 6

Identical to Procedure No. 2, except that the gelatinous slurry of Aerosil, ammonium heptamolybdate and TeO$_2$ was boiled for 1½ hours, then cooled to 70° C. before adding the H$_3$PO$_4$ and Sb$_2$O$_3$.

TABLE III

C$_3$=-Ammoxidation Over Sb$_{10}$Mo$_{0.3}$Te$_{0.1}$P$_{9.7}$O$_x$ + 20% SiO$_2$
Effect of Prep. Procedure, Mo-Source, and Silica Support
CT = 6 sec.; C$_3$/NH$_3$/O$_2$/H$_2$O = 1.0/1.2/2.0/3.3

| Example | Prep Proc | Mo[1] Source | Sup[2] | Heat Treat (°C.) | Rx T (°C.) | Surface Area m$^2$/g | CT sec | % Conv C$_3$ | % Yields AN | Aceto | HCN | CO$_x$ | % Select AN | Perform Number |
|---|---|---|---|---|---|---|---|---|---|---|---|---|---|---|
| 33 | 1 | PMA | A | 525 | 420 | 47.9 | 6 | 97.9 | 69.6 | 9.1 | 4.1 | 14.7 | 71.0 | 70 |
| 34 | 1 | PMA | A | 525 | 420 | | 9 | 96.9 | 64.6 | 7.9 | 3.3 | 17.8 | 66.7 | 66 |
| 35 | 1 | AHM | A | 525 | 420 | | 6 | 100.0 | 63.9 | 11.0 | 3.5 | 19.7 | 63.9 | 64 |
| 36 | 1 | AHM | A | 525 | 405 | | 6 | 95.7 | 55.0 | 13.4 | 4.9 | 17.3 | 57.5 | 56 |
| 37 | 1 | AHM | A | 525 | 405 | | 9 | 97.2 | 56.3 | 14.9 | 4.5 | 18.2 | 57.8 | 57 |
| 38 | 1 | AHM | A | 600 | 420 | | 6 | 93.4 | 56.9 | 15.9 | 4.0 | 13.8 | 60.9 | 59 |
| 39 | 2 | PMA | A | 525 | 420 | 45.3 | 6 | 79.4 | 56.8 | 7.9 | 4.1 | 10.1 | 71.6 | 64 |
| 40 | 2 | AHM | A | 525 | 420 | 46.4 | 6 | 90.0 | 65.7 | 8.5 | 3.8 | 11.4 | 72.9 | 69 |
| 41 | 2 | AHM | A | 525 | 420 | 46.4 | 9 | 86.5 | 63.7 | 6.6 | 4.0 | 11.6 | 73.6 | 69 |
| 42 | 2 | AHM | A | 525 | 460 | 46.4 | 6 | 88.6 | 69.0 | 4.7 | 3.0 | 10.7 | 77.8 | 73 |
| 43 | 2 | AHM | A | 525 | 460 | 47.4 | 6 | 83.8 | 61.3 | 3.0 | 3.0 | 11.2 | 73.1 | 67 |
| 44 | 3 | AHM | A | 525 | 460 | 46.8 | 6 | 47.9 | 32.9 | 2.3 | 1.4 | 8.4 | 68.6 | 51 |
| 45 | 4 | AHM | A | 525 | 460 | 44.6 | 6 | 48.9 | 36.3 | 1.8 | 1.1 | 7.6 | 74.2 | 55 |
| 46 | 5 | AHM | A | 525 | 460 | 46.6 | 6 | 81.4 | 49.7 | 2.9 | 2.3 | 12.7 | 61.0 | 55 |
| 47 | 6 | AHM | A | 525 | 460 | 45.2 | 6 | 65.2 | 35.7 | 2.2 | 1.1 | 10.5 | 54.8 | 45 |
| 48 | 2 | AHM | D | 525 | 420 | | 6 | 61.6 | 45.3 | 6.1 | 3.7 | 6.0 | 73.6 | 59 |

TABLE III-continued $C_3^=$-Ammoxidation Over $Sb_{10}Mo_{0.3}Te_{0.1}P_{9.7}O_x$ + 20% $SiO_2$
Effect of Prep. Procedure, Mo-Source, and Silica Support
CT = 6 sec.; $C_3/NH_3/O_2/H_2O$ = 1.0/1.2/2.0/3.3

| Example | Prep Proc | Mo[1] Source | Sup[2] | Heat Treat (°C.) | Rx T (°C.) | Surface Area m²/g | CT sec | % Conv $C_3$ | % Yields AN | Aceto | HCN | $CO_x$ | % Select AN | Perform Number |
|---|---|---|---|---|---|---|---|---|---|---|---|---|---|---|
| 49[3] | 2 | AHM | A | 525 | 460 | | 6 | 89.4 | 63.4 | 4.0 | 4.8 | 12.6 | 70.9 | 67 |
| 50 | 2 | AHM | C | 525 | 460 | 20.5 | 6 | 74.4 | 59.1 | 3.6 | 2.4 | 7.2 | 79.5 | 69 |
| 51 | 2 | AHM | C | 525 | 460 | 22.2 | 6 | 78.9 | 57.5 | 4.4 | 3.8 | 11.1 | 72.9 | 65 |
| 52 | 2 | AHM | B | 525 | 460 | 15.8 | 6 | 71.2 | 43.0 | 2.3 | 1.6 | 9.5 | 60.4 | 52 |
| 53[4] | 2 | AHM | B | 525 | 460 | 18.4 | 6 | 67.1 | 31.6 | 1.1 | 1.3 | 13.4 | 47.1 | 39 |

[1]PMA = phosphomolybdic acid
AHM = ammonium heptamolybdate
[2]A = Aerosil 200
B = Aerosil OX50 (low surface area)
C = Aerosil R972 ("methylated")
D = Large-pore silica, Alfa Inorganics #89384
[3]Promoted cat. $Sb_{9.9}Co_{0.1}Fe_{0.1}Te_{0.1}Mo_{0.3}P_{9.6}O_x$ + 20% $SiO_2$
[4]Promoted cat. $Sb_{9.9}Fe_{0.1}Te_{0.1}Mo_{0.3}P_{9.6}O_x$ + 20% $SiO_2$ The above Examples 33 to 53 show that catalysts having significant activity in the production of acrylonitrile can be produced by a wide variety of different methods using different types of support and different molybdenum sources. In addition, this data shows that catalysts with better properties can be produced with the highest degree of reproducibility using Procedure No. 2 with ammonium heptamolybdate as the molybdenum source.

Examples 54 to 68 set forth in the following Table IV show the effect of various different promoters on tellurium-containing catalysts of the present invention.

TABLE IV $SbPO_4$-Based Catalysts Containing Mo and Te, with 20% Aerosil 200
Effect of Promoters
Cal. Temp. 525° C.; CT = 6 sec., $C_3/NH_3/O_2/H_2O$ = 1.0/1.2/2.0/3.3
Mo Source = AHM; Prep. Procedure = 2

| Example | Catalyst Composition | Surface Area m²/g | Rx T (°C.) | % Conv $C_3$ | % Yields AN | Aceto | HCN | $CO_x$ | % Select AN | PN[2] |
|---|---|---|---|---|---|---|---|---|---|---|
| 54 | $Sb_{10}Mo_{0.3}Te_{0.1}P_{9.7}O_x$ | 46.4 | 460 | 88.6 | 69.0 | 4.7 | 3.0 | 10.7 | 77.8 | 73 |
| 55 | $Li_{0.1}Sb_{10}Te_{0.1}P_{9.7}O_x$ | | 420 | 89.8 | 62.9 | 10.0 | 4.0 | 12.3 | 70.1 | 67 |
| 56 | " | | 460 | 91.2 | 70.6 | 4.0 | 3.9 | 11.9 | 77.4 | 74 |
| 57 | $Na_{0.05}Sb_{10}Mo_{0.3}Te_{0.1}P_{9.7}O_x$ | | 420 | 88.3 | 64.8 | 8.5 | 4.4 | 10.0 | 73.4 | 69 |
| 58 | " | | 460 | 83.2 | 62.8 | 4.4 | 3.2 | 11.7 | 75.4 | 69 |
| 59 | $K_{0.05}Sb_{10}Mo_{0.3}Te_{0.1}P_{9.7}O_x$ | | 420 | 74.6 | 57.1 | 6.2 | 3.8 | 7.0 | 76.5 | 67 |
| 60 | " | | 460 | 67.2 | 52.1 | 2.0 | 2.4 | 9.4 | 77.5 | 65 |
| 61 | $Cs_{0.05}Sb_{10}Mo_{0.3}Te_{0.1}P_{9.7}O_x$ | | 520 | 66.1 | 50.1 | 5.3 | 3.7 | 6.6 | 75.8 | 63 |
| 62 | " | | 460 | 63.4 | 51.0 | 1.7 | 2.1 | 7.7 | 80.4 | 66 |
| 63 | $Sb_{9.9}Mo_{0.3}Te_{0.1}Co_{0.1}P_{9.6}O_x$ | 47.1 | 460 | 85.6 | 67.1 | 4.6 | 2.3 | 9.8 | 78.4 | 73 |
| 64 | " | | 460 | 82.3 | 61.5 | 4.7 | 3.4 | 11.6 | 74.8 | 68 |
| 65 | $Sb_{9.9}Mo_{0.6}Te_{0.2}Co_{0.2}P_{9.5}O_x$ | | 460 | 67.4 | 31.9 | 1.7 | 1.0 | 13.1 | 47.2 | 40 |
| 66 | $Sb_{9.9}Mo_{0.3}Te_{0.1}Fe_{0.1}P_{9.6}O_x$ | 48.7 | 460 | 84.7 | 67.2 | 3.3 | 3.6 | 8.7 | 79.4 | 73 |
| 67 | " | | 460 | 88.9 | 64.8 | 4.3 | 3.7 | 16.5 | 72.9 | 69 |
| 68 | $Sb_{9.9}Mo_{0.3}Te_{0.1}Fe_{0.1}Co_{0.1}P_{9.6}O_x$ | | 460 | 89.4 | 63.4 | 4.0 | 4.8 | 12.6 | 70.9 | 67 |

The above Examples 54 to 68 show that a wide variety of different elements exhibit a promoting effect on the molybdenum and tellurium-containing antimony phosphate oxide complex catalysts of the invention.

Although only a few embodiments of the present invention have been described above, many modifications can be made without departing from the spirit and scope of the invention. All such modifications are intended to be included within the scope of the present invention, which is to be limited only by the following claims.

We claim:

1. In an ammoxidation process for producing acrylonitrile or methacrylonitrile in which a reactant selected from the group consisting of propylene and isobutylene together with oxygen and ammonia in the vapor phase are contacted with a catalyst at elevated temperature, the improvement wherein said catalyst is a copper-free antimony phosphate oxide complex, at least 80% of said oxide complex exhibiting the antimony phosphate layer structure, the Sb/P ratio of said oxide complex being between 0.8/1 and 1/0.8, substantially all of the antimony in said oxide complex being in the trivalent state, said oxide complex having the formula:

$$A_aB_bSb_cMo_dTe_mBi_nP_pO_x$$

wherein

A is one or more elements selected from the group of alkali metals, alkaline earth metals and thallium;
B is one or more elements selected from the group of Fe, Co, Ni, Mn, Cr, Zn, Cd and B; and wherein
a is 0–1;
b is 0–1;
c is 8–10;
d is 0.1–2;
p is 7.0–9.9;
m is >0–1;
n is 0–1;
(m+n)>0;
d/m is 1–20;
d+m is 0.2–1.0; and x is a number which satisfies the valence requirements of the other elements present.

2. The process of claim 1 wherein said catalyst is supported on a silica support.

3. The process of claim 2 wherein said catalyst is made with dry colloidal silica.

4. The process of claim 1 wherein said oxide complex is free of Fe.

5. The process of claim 1 wherein said oxide complex contains about 0.1 atoms Fe based on 9.9 atoms Sb.

* * * * *